(12) United States Patent  
Ito et al.

(10) Patent No.: US 7,025,728 B2
(45) Date of Patent: Apr. 11, 2006

(54) METHOD FOR REDUCING NOISE, AND PULSE PHOTOMETER USING THE METHOD

(75) Inventors: Kazumasa Ito, Tokyo (JP); Masaru Yarita, Tokyo (JP); Tetsuya Shibasaki, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 114 days.

(21) Appl. No.: 10/660,557

(22) Filed: Sep. 12, 2003

(65) Prior Publication Data

US 2004/0267140 A1 Dec. 30, 2004

(30) Foreign Application Priority Data

Jun. 30, 2003 (JP) .......................... P2003-187324

(51) Int. Cl.
*A61B 5/02* (2006.01)
*A61B 5/00* (2006.01)

(52) U.S. Cl. ...................... 600/500; 600/336; 600/324

(58) Field of Classification Search ........ 600/500–503, 600/310, 326, 322–324, 330, 336, 504, 507
See application file for complete search history.

(56) References Cited

U.S. PATENT DOCUMENTS

| | | | |
|---|---|---|---|
| 5,355,882 A * | 10/1994 | Ukawa et al. .............. 600/323 |
| 5,482,036 A | 1/1996 | Diab et al. | |
| 5,490,505 A | 2/1996 | Diab et al. | |
| 5,632,272 A | 5/1997 | Diab et al. | |
| 5,685,299 A | 11/1997 | Diab et al. | |
| 5,690,104 A | 11/1997 | Kanemoto et al. | |
| 5,769,785 A | 6/1998 | Diab et al. | |
| 6,002,952 A * | 12/1999 | Diab et al. .................. 600/310 |
| 6,036,642 A | 3/2000 | Diab et al. | |
| 6,067,462 A | 5/2000 | Diab et al. | |
| 6,081,735 A | 6/2000 | Diab et al. | |
| 6,083,172 A * | 7/2000 | Baker et al. ................ 600/500 |
| 6,157,850 A | 12/2000 | Diab et al. | |
| 6,206,830 B1 | 3/2001 | Diab et al. | |
| 6,236,872 B1 | 5/2001 | Diab et al. | |
| 6,263,222 B1 | 7/2001 | Diab et al. | |
| 6,453,184 B1 * | 9/2002 | Hyogo et al. ............... 600/323 |
| 6,501,975 B1 | 12/2002 | Diab et al. | |
| 6,780,158 B1 * | 8/2004 | Yarita ........................ 600/500 |

FOREIGN PATENT DOCUMENTS

| JP | 3-270917 B2 | 1/2001 |
|---|---|---|
| JP | 3270917 B2 | 1/2002 |

* cited by examiner

*Primary Examiner*—Robert L. Nasser
*Assistant Examiner*—Navin Natnithithadha
(74) *Attorney, Agent, or Firm*—Sughrue Mion, PLLC

(57) ABSTRACT

A living body is irradiated with a first light beam having a first wavelength and a second light beam having a second wavelength which is different from the first wavelength. The first light beam and the second light beam, which have been reflected or transmitted from the living body, are converted into a first electric signal corresponding to the first wavelength and a second electric signal corresponding to the second wavelength, as the observed pulse data. A light absorbance ratio obtained from the first electric signal and the second electric signal is computed, for each one of frequency ranges dividing an observed frequency band. It is determined that noise is not mixed into the observed pulse wave data in a case where a substantial match exists among light absorbance ratios computed for the respective frequency ranges.

14 Claims, 10 Drawing Sheets

| FREQUENCY RANGE | LIGHT ABSORBANCE RATIO 1 | LIGHT ABSORBANCE RATIO 2 |
|---|---|---|
| 0.5 - 1.0Hz | 0.52 | 0.62 |
| 1.0 - 1.5Hz | 0.49 | 0.75 |
| 1.5 - 2.0Hz | 0.59 | 0.68 |
| 2.0 - 2.5Hz | 0.71 | 0.85 |
| 2.5 - 3.0Hz | 0.55 | 0.85 |
| 3.0 - 3.5Hz | 0.83 | 0.99 |
| 3.5 - 4.0Hz | 0.81 | 0.90 |
| 4.0 - 4.5Hz | 0.82 | 0.87 |
| 4.5 - 5.0Hz | 0.81 | 0.90 |
| 5.0 - 5.5Hz | 0.82 | 0.97 |
| 5.5 - 6.0Hz | 0.83 | 0.92 |

FIG. 10

| FREQUENCY RANGE | LIGHT ABSORBANCE RATIO 1 | LIGHT ABSORBANCE RATIO 2 |
|---|---|---|
| 0.5 - 1.0Hz | 0.45 | 1.14 |
| 1.0 - 1.5Hz | 0.49 | 0.57 |
| 1.5 - 2.0Hz | 0.50 | 0.88 |
| 2.0 - 2.5Hz | 0.49 | 0.56 |
| 2.5 - 3.0Hz | 0.49 | 0.57 |
| 3.0 - 3.5Hz | 0.48 | 0.60 |
| 3.5 - 4.0Hz | 0.50 | 0.58 |
| 4.0 - 4.5Hz | 0.52 | 0.59 |
| 4.5 - 5.0Hz | 0.50 | 0.58 |
| 5.0 - 5.5Hz | 0.50 | 0.58 |
| 5.5 - 6.0Hz | 0.51 | 0.61 |

FIG. 11

METHOD FOR REDUCING NOISE, AND PULSE PHOTOMETER USING THE METHOD

BACKGROUND OF THE INVENTION

The invention relates to a device for measuring physiological information through use of photoplethysmograms measured at a plurality of wavelengths, and more particularly, to an improvement in a pulse photometer used for diagnosing a problem in a respiratory system or a circulatory system.

A known technique for measuring a concentration of light absorbing materials contained in blood during medical care is pulse photometry intended for measuring an oxygen saturation $SpO_2$, the concentration of abnormal hemoglobin such as carboxyhemoglobin (COHb) and methemoglobin (MetHb), or a concentration of injected pigment. A device for measuring oxygen saturation $SpO_2$ in particular is called a pulse oximeter.

The principle of the pulse oximeter is to irradiate onto living tissue light rays of a plurality of wavelengths exhibiting different light absorbing characteristics with respect to a material of interest and to determine the concentration of the material on the basis of a pulse wave produced through consecutive measurement of quantity of transmitted light.

Japanese Patent No. 3270917 (cf., claims 1, 2 and FIGS. 2 and 4) discloses determination of a saturation level of oxygen in arterial blood and a concentration of light-absorbing materials in the same by: emitting two light-rays of different wavelengths onto living tissue; plotting graphs with levels of the resultant two pulse waves originating from transmitted light being taken as vertical and horizontal axes, respectively, to thereby determine regression lines; and determining the oxygen saturation and the concentration of light-absorbing materials in the arterial blood on the basis of gradients of the regression lines. This technique enhances measurement accuracy and reduces power consumption.

However, a large amount of computing operation is still required to determine regression lines and gradients thereof through use of many sampled data sets pertaining to pulse waves of respective wavelengths.

The principle will now be described by taking, as an example, a pulse oximeter for measuring the oxygen saturation in arterial blood.

This technique is not limited to a pulse oximeter but is also applicable to a device (or a pulse photometer) which, on the basis of the principle of the pulse photometry, measures abnormal hemoglobin (carboxyhemoglobin or methemoglobin) or a light absorbing material in blood such as pigment injected in blood.

Figure 1:
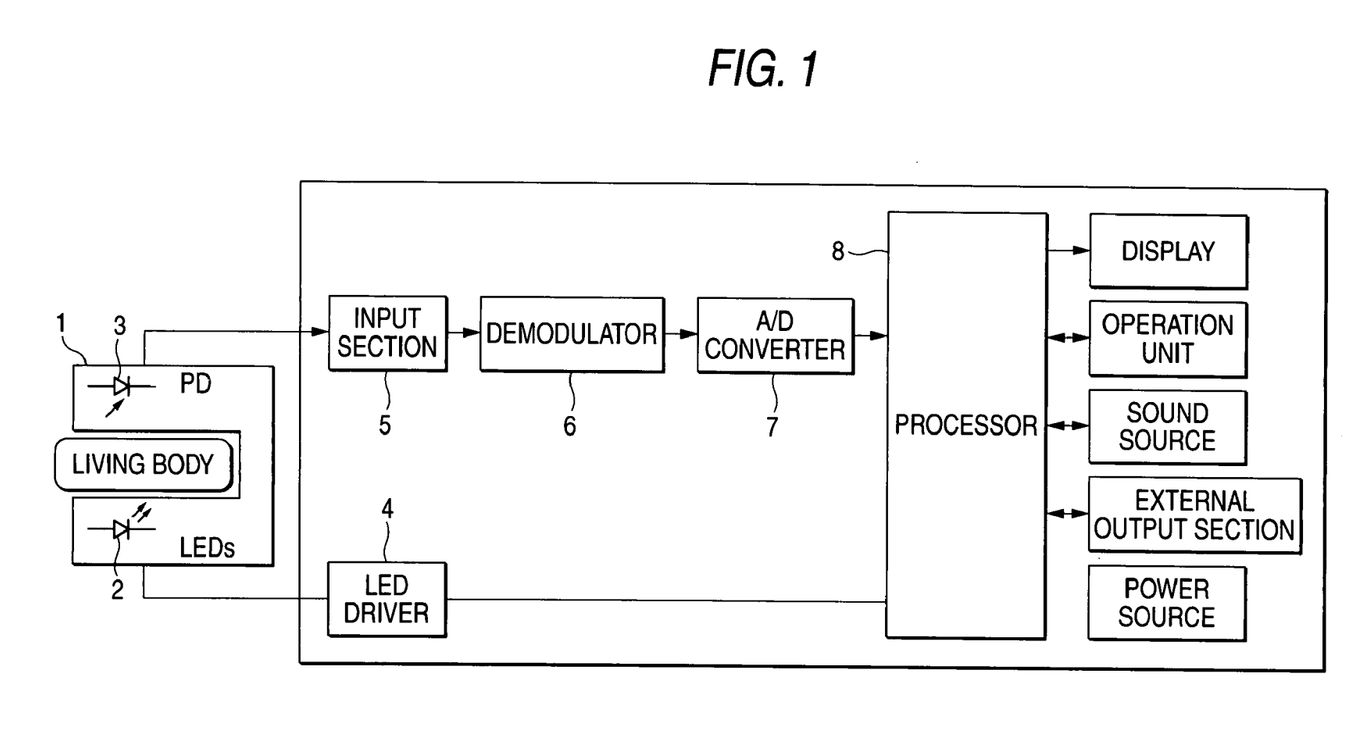
FIG. 1 is a block diagram showing the configuration of a pulse oximeter according to one embodiment of the invention.

FIG. 1 is a block diagram of such a pulse oximeter. The device will now be described by taking the pulse oximeter as an example.

At the time of measurement, a probe 1 is usually attached to an area subjected to the measurement.

A processor 8 produces light emission timings for a light emitter (LEDs) 2 which produce light rays of different wavelengths, that is, a red-light emitting diode (hereinafter abbreviated "R-LED") and an infrared-light-ray emitting diode (hereinafter abbreviated "IR-LED"). The R-LED and the IR-LED, both being provided in the probe 1, are driven by an LED driver 4, to thereby alternately emit light.

The light emitted by the LEDs 2 passes through the area subjected to the measurement to which the probe is attached, and is received by a light receiver (photo diode; PD) 3 provided in the probe 1.

The thus-received signal is converted from light into electricity by the light receiver 3 and is subsequently converted into a voltage by an input section 5.

Components reflecting optical characteristics of pulsation of the area subjected to the measurement appear in this signal in the form of AC components.

By a demodulator 6, the signal output from the light receiver (PD) 3 is separated and demodulated into a waveform of an infrared light ray (IR) and that of a red light ray (R). The waveforms are digitized into signal trains by an A/D converter 7. The signal trains are sent to the processor 8, where the signal trains are processed, thereby computing, e.g., oxygen saturation $SpO_2$.

The signal trains that have been digitized by the A/D converter 7 corresponding to infrared light (IR) and red light (R) form respective measured data sets.

Light absorbance A of the light that has passed through tissue is expressed by Equation (1), with the attenuation of light in blood being taken as Ab and the attenuation of light in other tissue being taken as At.

$$A = Ab + At = \ln(Iin) - \ln(Iout) = ECD + At \qquad (1)$$

wherein:
Iout: Intensity of transmitted light
Iin: Intensity of incident light
E: Absorption coefficient of blood
C: Concentration of hemoglobin in blood
D: Thickness of blood When the blood thickness has assumed $D+\Delta D$ as a result of pulsation of blood, Equation 1 is transformed as follows.

$$A + \Delta Ab = \ln(Iin) - \ln(Iout) + \Delta \ln(Iout) = EC(D+\Delta D) + At \qquad (2)$$

Subtracting Equation 1 from Equation 2, Equation 3 is obtained.

$$\Delta Ab = \Delta \ln(Iout) = EC\Delta D \qquad (3)$$

Equation 3 is defined for wavelengths $\lambda 1$, $\lambda 2$ as follows.

$$\Delta Ab_1 = -\Delta \ln(Iout_1) = E_1 C \Delta D \qquad (4)$$

$$\Delta Ab_2 = -\Delta \ln(Iout_2) = E_2 C \Delta D \qquad (5)$$

Subscripts 1, 2 indicate that the corresponding terms are relevant to wavelengths $\lambda_1$, $\lambda_2$. Provided that Equation 4/Equation 5=$\Phi s$, we have $$\Phi_s = \frac{\Delta Ab_1}{\Delta Ab_2} = \frac{\Delta \ln(Iout_1)}{\Delta \ln(Iout_2)} = \frac{E_1}{E_2} \qquad (6)$$

$\Phi$ is determined by measuring $\Delta \ln(Iout1)$, $\Delta \ln(Iout2)$, whereby the oxygen saturation is determined as follows.

$$SpO_2 = f(\Phi_s) \qquad (7)$$

When the influence of body movement or a like factor other than the component reflecting pulsation is superimposed on $\Delta \ln(Iout1)$, $\Delta \ln(Iout2)$, light absorbance of each of the wavelengths is defined as follows.

$$\Delta Ab_1' = -\Delta \ln(Iout_1') = E_1 C \Delta D + En_1 Cn \Delta Dn \qquad (8)$$

$$\Delta Ab_2' = -\Delta \ln(Iout_2') = E_2 C \Delta D + En_2 Cn \Delta Dn \qquad (9)$$

wherein:
En: Absorption coefficient of the noise source
Cn: Concentration of the noise source
Dn: Change in thickness of the noise source A waveform (pulse wave) reflecting a pulsation component is not solely obtained, and a signal on which noise is superimposed is observed. In this case, a light absorbance ratio Φ' is defined as follows:

$$\Phi' = \frac{\Delta Ab'_1}{\Delta Ab'_2} = \frac{\Delta \ln(Iout'_1)}{\Delta \ln(Iout'_2)} = \frac{E_1 C \Delta D + En_1 Cn \Delta Dn}{E_2 C \Delta D + En_2 Cn \Delta Dn} \quad (10)$$

Hence, the light absorbance ratio does not coincide with the oxygen saturation in arterial blood.

Figure 2A:
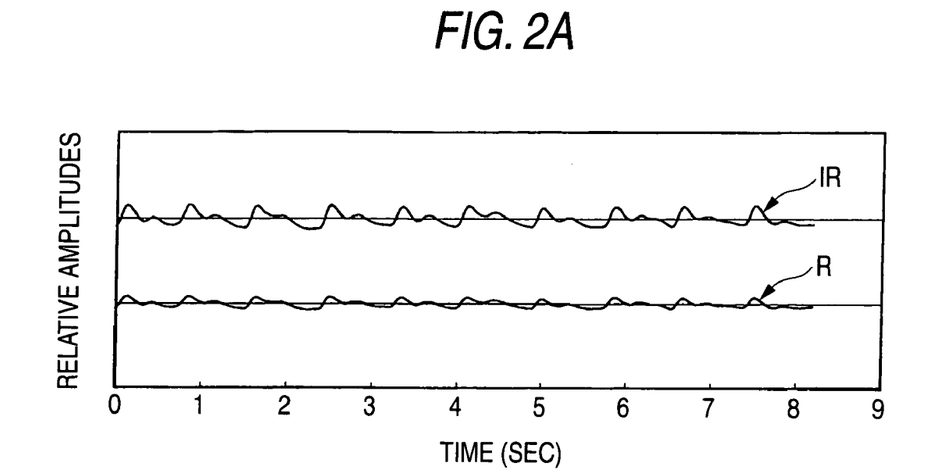
FIG. 2A is a waveform obtained through logarithmeric processing.

FIG. 2A shows waveforms which have been subjected to: processing in which transmitted light intensity data at respective wavelengths at predetermined time intervals are logarithmic-computed; and then a mean of the logarithmic-computed values is made to zero or high-pass filtering is performed with respect to the logarithmic-computed values.

Figure 2B:
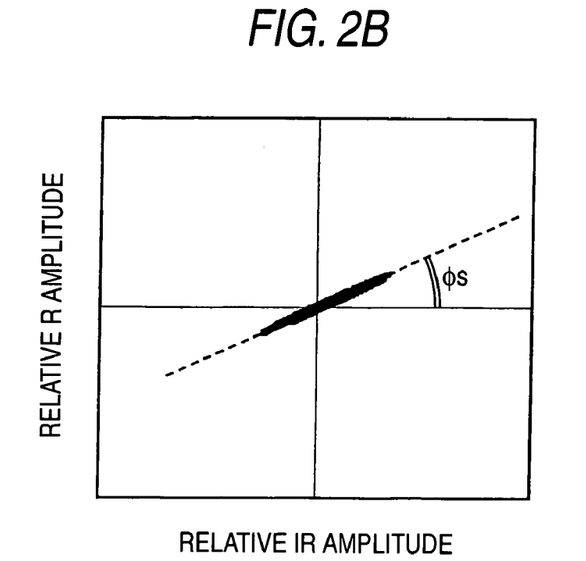
FIG. 2B is a graph plotted with the amplitude of infrared light being taken as a horizontal axis and the amplitude of red light being taken as a vertical axis.

FIG. 2B shows a graph through use of waveform data measured substantially at the same time when the waveforms shown in FIG. 2A are measured (the time is sufficiently shorter than the duration of a frequency component of a pulse wave) with the amplitude of infrared light being taken as a horizontal axis and the amplitude of red light being taken as a vertical axis.

If the observed data reflect a mere pulse wave component, the graph essentially assumes the shape of a straight line. The gradient of the straight line shows the light absorbance ratio Φs.

Figure 3A:
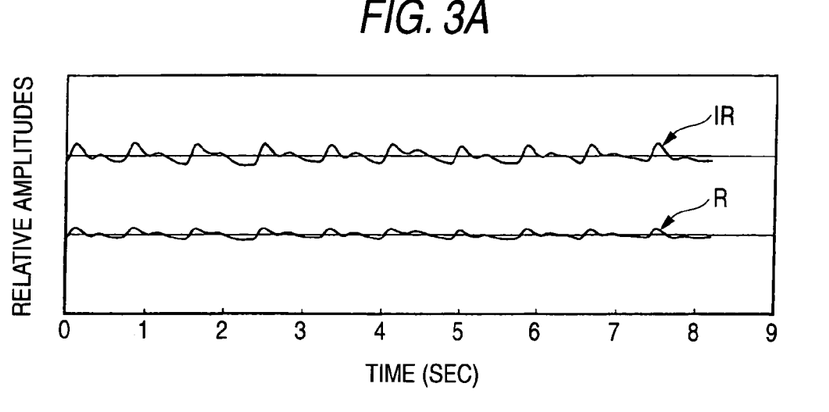
FIG. 3A shows observed (measured) waveforms on which noise is superimposed.
Figure 3B:
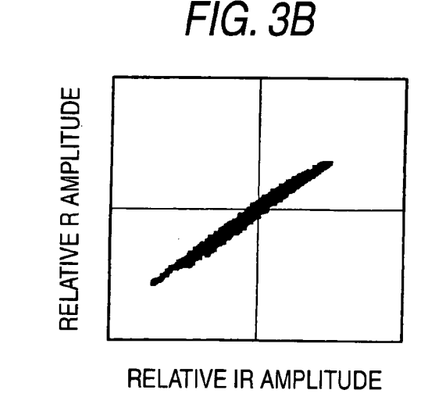
FIG. 3B is a graph plotted with the amplitude of the infrared light being taken as a horizontal axis and the amplitude of the red light being taken as the vertical axis.

However, when noise is superimposed on the data as shown in FIG. 3A, there is obtained a result Into which the light absorbance ratio of noise and the light absorbance ratio of pulsation are merged as shown in FIG. 3B, in contrast with the case of a pulse wave component.

As mentioned above, when measured pulse wave data include noise, an accurate light absorption ratio cannot be measured, and hence noise must be reduced.

Hitherto-known techniques for reducing this noise are a frequency analysis technique and an independent component analysis technique.

However, when the frequency of noise overlaps the fundamental wave of a signal component of measured pulse wave data or a harmonic wave of the same, the frequency analysis technique encounters difficulty in extracting a signal component.

According to the independent component analysis technique, an observed signal cannot be dissolved into independent components beyond measured waveform data. When a plurality of noise sources are present, difficulty is encountered in dissolving the data.

SUMMARY OF THE INVENTION

It is therefore an object of the invention to provide a method for determining a light absorbance ratio by readily reducing noise from an observation signal on which noise is superimposed, to thereby extract pulse wave data.

It is also an object of the invention to provide a pulse photometer using pulse wave data from which noise has been reduced by the above method.

In order to achieve the above objects, according to the invention, there is provided a method of processing an observed pulse wave data, comprising steps of:

irradiating a living body with a first light beam having a first wavelength and a second light beam having a second wavelength which is different from the first wavelength;

converting the first light beam and the second light beam, which have been reflected or transmitted from the living body, into a first electric signal corresponding to the first wavelength and a second electric signal corresponding to the second wavelength, as the observed pulse data;

computing a light absorbance ratio obtained from the first electric signal and the second electric signal, for each one of frequency ranges dividing an observed frequency band; and determining that noise is not mixed into the observed pulse wave data in a case where a substantial match exists among light absorbance ratios computed for the respective frequency ranges.

Preferably, the existence of the substantial match of the light absorbance ratios is determined with regard to frequency ranges in which at least one of the first electric signal and the second electric signal has relatively large powers.

According to the invention, there is also provided a method of processing an observed pulse wave data, comprising steps of:

irradiating a living body with a first light beam having a first wavelength and a second light beam having a second wavelength which is different from the first wavelength;

converting the first light beam and the second light beam, which have been reflected or transmitted from the living body, into a first electric signal corresponding to the first wavelength and a second electric signal corresponding to the second wavelength, as the observed pulse data; and whitening the first electric signal and the second electric signal by an affine transformation using a known light absorbance ratio, in order to separate a pulse signal component and a noise component which are contained in the observed pulse data.

Preferably, the affine transformation is performed with the following equation:

$$\begin{pmatrix} S \\ N \end{pmatrix} = \begin{pmatrix} 1 & -\frac{1}{\tan\theta} \\ 0 & \frac{1}{\sin\theta} \end{pmatrix} \begin{pmatrix} \cos\phi & \sin\phi \\ -\sin\phi & \cos\phi \end{pmatrix} \begin{pmatrix} s1 \\ s2 \end{pmatrix}$$

where, S is the pulse signal component N is the noise component, s1 is the first electric signal, s2 is the second electric signal, $\phi = \text{Tan}^{-1} \Phi$, Φ is the known light absorbance ratio, and θ is a value selected from a range of $-\phi$ to $(\pi/2-\phi)$, and wherein θ is so selected as to make a norm of the pulse signal component minimum.

Here, it is preferable that the signal processing method further comprises steps of:

computing a light absorbance ratio obtained from the first electric signal and the second electric signal, for each one of frequency ranges dividing an observed frequency band; and determining that noise is not mixed into the observed pulse wave data in a case where a substantial match exists among light absorbance ratios computed for the respective frequency ranges.

Here, one of the light absorbance ratios, which are determined that the noise is not mixed therein, is used as the known light absorbance ratio.

Preferably, the signal processing method further comprises a step of obtaining a signal-to-noise ratio of the observed pulse wave data by performing a frequency analysis with respect to the pulse signal component and the noise component at each of predetermined frequencies.

Preferably, the signal processing method further comprises a step of displaying a pulse wave of the living body, based on the pulse signal component.

Preferably, the signal processing method further comprises a step of calculating a pulse rate of the living body based on the pulse signal component.

According to the invention, there is also provided a method of processing an observed pulse wave data, comprising steps of:

irradiating a living body with a first light beam having a first wavelength and a second light beam having a second wavelength which is different from the first wavelength;

converting the first light beam and the second light beam, which have been reflected or transmitted from the living body, into a first electric signal corresponding to the first wavelength and a second electric signal corresponding to the second wavelength, as the observed pulse data;

whitening the first electric signal and the second electric signal to separate a pulse signal component and a noise component which are contained in the observed pulse data, for each one of frequency ranges dividing an observed frequency band.

Preferably, the step of whitening the first electric signal and the second electric signal is performed with independent component analysis.

Preferably, the signal processing method further comprises a step of obtaining a signal-to-noise ratio of the observed pulse wave data by performing a frequency analysis with respect to the signal component and the noise component at each one of the frequency ranges.

According to the invention, there is also provided a pulse photometer in which each of the signal processing methods is executed.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE INVENTION (How to Separate Signal Component from Noise Component by Utilization of Known Light Absorbance Ratio)

First, the light received by the light receiver 3 provided in the probe 1 having such a configuration as that shown in FIG. 1 is converted into a voltage by the input section 5.

A component reflecting an optical characteristic of pulsation arising in an area subjected to the measurement appears in the received light signal as an AC component.

The signal output from the light receiver 3 is separated and demodulated into a waveform of infrared light (IR) and a waveform of red light (R) by the demodulator 6, and the waveforms are digitized by the A/D converter 7.

A data sequence of the infrared light observation signal IR, a data sequence of the red light observation signal R, pulse wave components of the observation signal S, and noise components of the observation signal N are respectively taken as:

$$IR = \{IR_i; i=0, 1, 2, \ldots\} \quad (11)$$

$$R = \{R_i; i=0, 1, 2, \ldots\} \quad (12)$$

$$S = \{S_i; i=0, 1, 2, \ldots\} \quad (13)$$

$$N = \{N_i; i=0, 1, 2, \ldots\} \quad (14)$$

Figure 4:
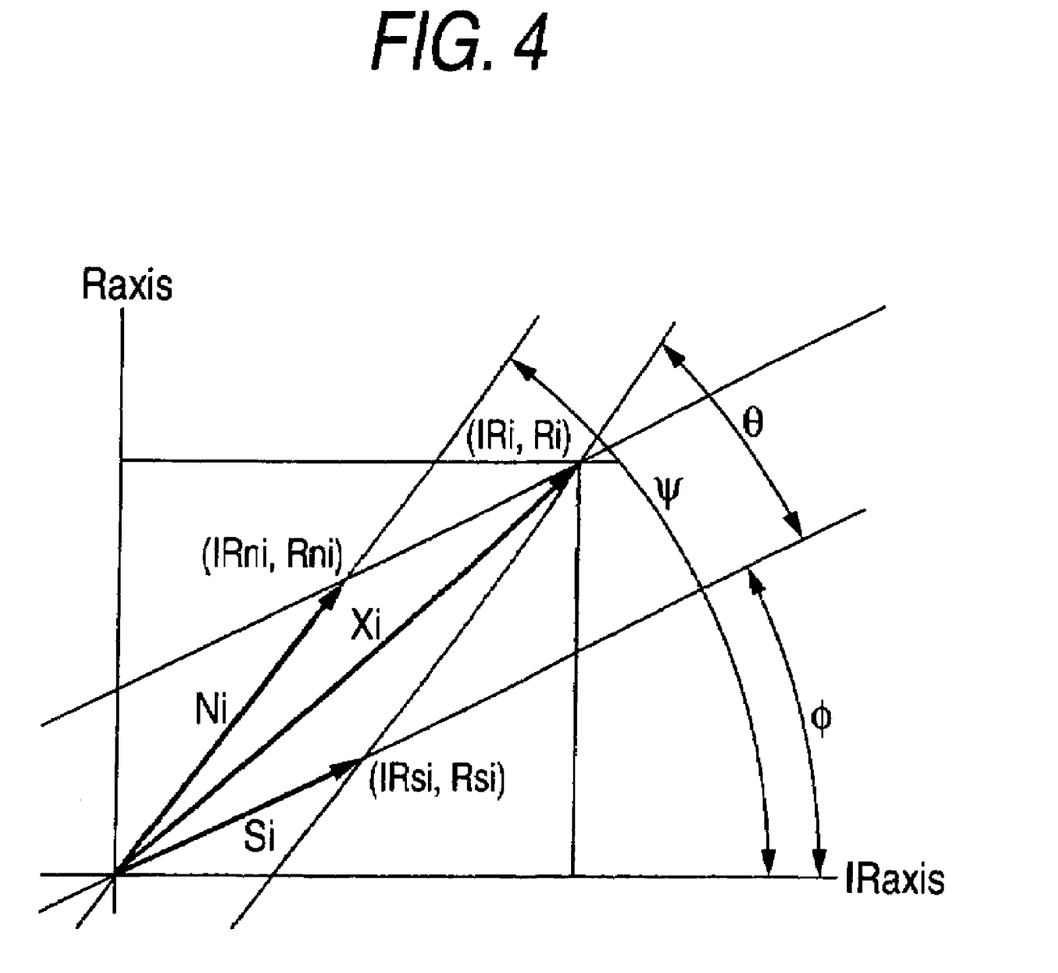
FIG. 4 is a view showing the relationship between a signal component and a noise component.

As shown in FIG. 4, provided that the gradient of the pulse wave component is taken as $\phi$ and the gradient of the noise component is taken as $\varphi$, the resultant observation signals ($IR_i$, $R_i$) are expressed as the sum of vectors, i.e., a signal component $S_i$ and a noise component $N_i$, as follows:

$$\begin{pmatrix} IR_i \\ R_i \end{pmatrix} = \begin{pmatrix} \cos\phi & \cos\varphi \\ \sin\phi & \sin\varphi \end{pmatrix} \begin{pmatrix} S_i \\ N_i \end{pmatrix} \quad (15)$$

Here, defining a matrix W as:

$$W = \begin{pmatrix} \cos\phi & \cos\varphi \\ \sin\phi & \sin\varphi \end{pmatrix} \quad (16)$$

If a transformation matrix A which is an inverse matrix of W can be caused to act on observation data, the signal component S can be separated from the noise component N as represented below.

$$\begin{pmatrix} S_i \\ N_i \end{pmatrix} = A \begin{pmatrix} IR_i \\ R_i \end{pmatrix} \quad (17)$$

This means that the signal component S is converted into a horizontal axis and the noise component N is converted into a vertical axis. The transformation matrix A to be used for implementing whitening is determined as:

$$A = \begin{pmatrix} \cos\phi & \cos\varphi \\ \sin\phi & \sin\varphi \end{pmatrix}^{-1} \quad (18)$$

$$= \frac{1}{\sin(\varphi - \phi)} \begin{pmatrix} \sin\varphi & -\cos\varphi \\ -\sin\phi & \cos\phi \end{pmatrix}$$

$$= \begin{pmatrix} 1 & -\frac{1}{\tan\theta} \\ 0 & \frac{1}{\sin\theta} \end{pmatrix} \begin{pmatrix} \cos\phi & \sin\phi \\ -\sin\phi & \cos\phi \end{pmatrix}$$

Therefore, we have:

$$\begin{pmatrix} S \\ N \end{pmatrix} = \begin{pmatrix} 1 & -\frac{1}{\tan\theta} \\ 0 & \frac{1}{\sin\theta} \end{pmatrix} \begin{pmatrix} \cos\phi & \sin\phi \\ -\sin\phi & \cos\phi \end{pmatrix} \begin{pmatrix} IR \\ R \end{pmatrix} \quad (19)$$

The light absorbance ratio $\Phi$ designates the gradient of a signal component. The relationship existing between the gradient $\phi$ and the light absorbance ratio $\Phi$ is expressed as $\Phi=\tan\phi$.

If a period of time is sufficiently shorter than the duration of a pulse rate, an immediately preceding value (e.g., a value obtained 10 msec previously) can be taken as a known value of $\Phi$. Alternatively, the light absorbance ratio which has been determined that the noise is not mixed therein is used as the known value of $\Phi$. Still alternatively, a candidate for $\phi$ obtained by the technique described later can also be employed.

Next, $\theta$ is expressed as:

$$\theta = \phi - \phi \quad (20)$$

Since $\phi$ is unknown, $\theta$ is determined as an angle at which a norm in the direction of the horizontal axis becomes minimum between $-\phi$ to $(\pi/2-\phi)$.

When the observation signal is processed through use of the transformation matrix A using the thus-obtained $\phi$, $\theta$, a signal component appears along the horizontal axis, and the noise component appears along the vertical axis.

Figure 3C:
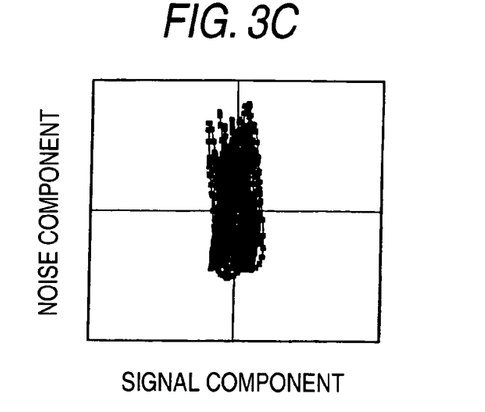
FIG. 3C is a graph obtained by subjecting the graph shown in FIG. 3B to processing performed by the transformation matrix A.

More specifically, the determinant expressed as Equation 19 means a coordinate transformation from a first coordinate system in which the observed signals IR and R are selected as the coordinate axes shown in FIG. 3B, to a second coordinate system in which the signal component and the noise component are selected as the coordinate axes shown in FIG. 3C.

FIG. 4 shows observed values (IRi, Ri) at a certain time point t=ti. The vector Xi representing the observed values is a synthesis vector of a signal component vector Si and a noise component vector Ni. Upon performing the above coordinate transformation, the signal component vector Si is first operated to be made coincident with the horizontal axis of the second coordinate system. Namely, the vector Si shown in FIG. 4 is rotated clockwise by an angle of $\phi$. The value of $\phi$ is obtained through the above relationship using the known value of $\Phi$.

The coefficient $\theta$ in Equation 19 corresponds to an operation to make the noise component vector Ni coincident with the vertical axis of the second coordinate system. Since the waveform shown in FIG. 3B is a set of the observed values, if the values of $\phi$ are made constant for the observed values at any of the time points, the values of $\theta$ accordingly vary corresponding to the respective time points. In order to uniquely determine the value of $\theta$ as the coefficient, dispersion of values (norm) in the horizontal axis (signal component) direction is checked while varying the value of $\theta$ within a range from $-\phi$ to $(\pi/2-\phi)$. The value of $\theta$ is finally determined as a value making the norm minimum.

Figure 3D:
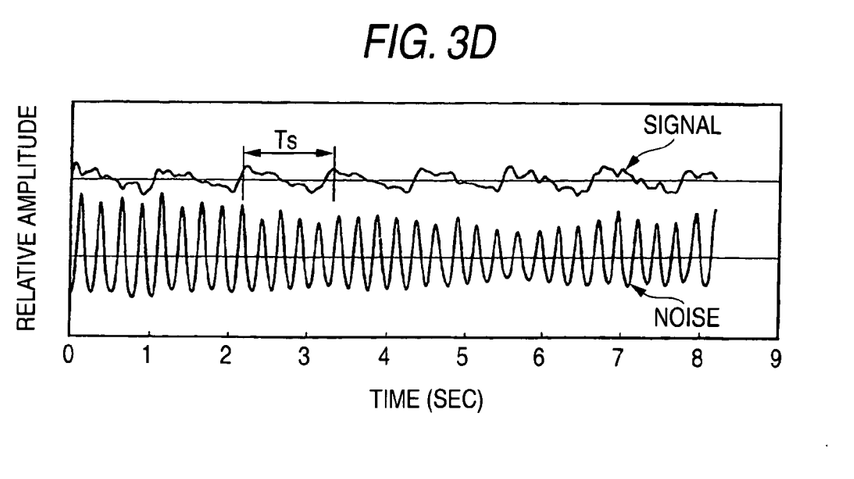
FIG. 3D is a waveform whose noise has been separated or reduced through the processing.

FIG. 3C shows a graph obtained by subjecting the graph shown in FIG. 3B to processing performed by the transformation matrix A. Further, FIG. 3D shows a waveform from which noise has been separated through the processing.

Figure 5:
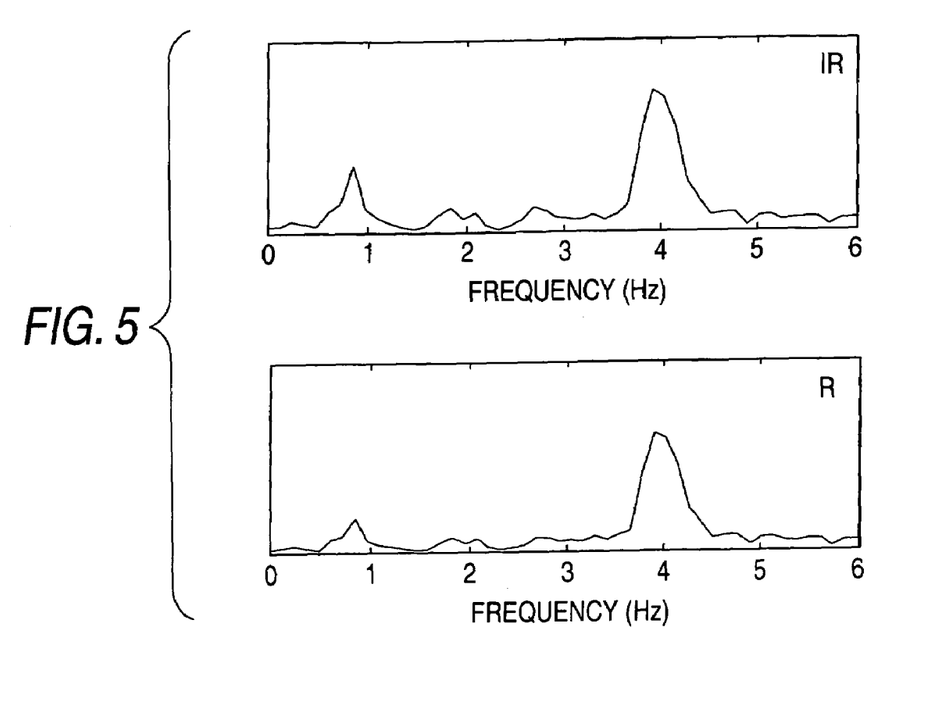
FIG. 5 is a view showing an infrared light spectrum and a red light spectrum, both obtained through frequency analysis performed with respect to the waveforms shown in FIG. 3A.
Figure 6:
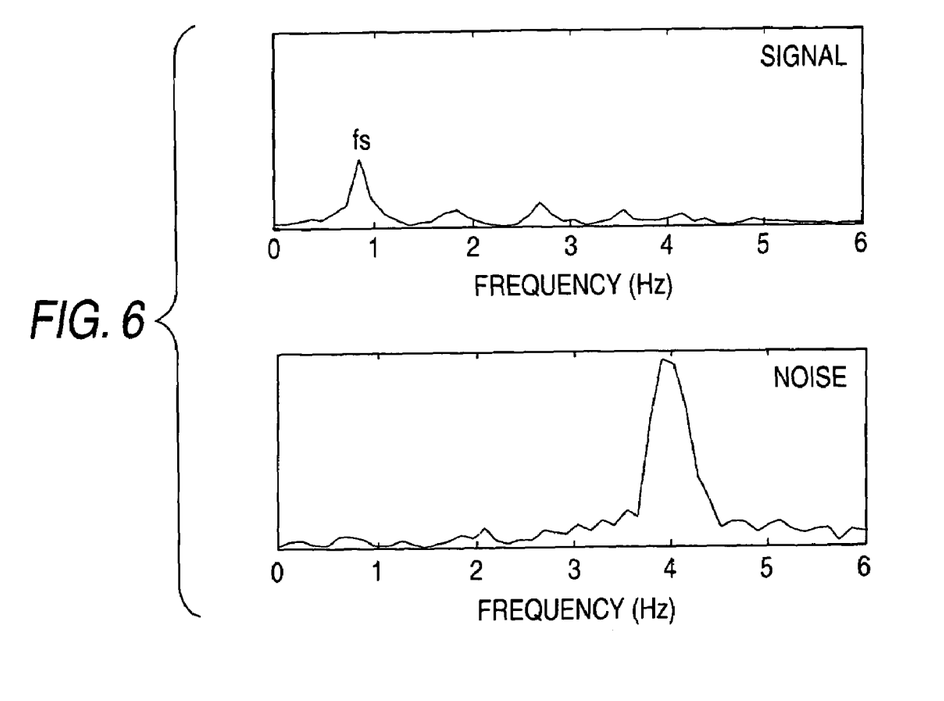
FIG. 6 is a view showing a spectrum obtained through frequency analysis of the signal component and the noise component shown in FIG. 3D.

FIG. 5 shows an infrared-ray spectrum (IR) and a red light spectrum (R), both being obtained through frequency analysis performed before processing, and FIG. 6 shows a spectrum obtained through frequency analysis of a signal component and a noise component performed after corresponding processing.

(How to Calculate Pulse Rate)

A peak-to-peak interval Ts (FIG. 3D) is obtained from the signal waveform extracted through the foregoing conversion processing, whereby a pulse rate=1/Ts×60 [beats/min.] can be readily determined.

Alternatively, the fundamental frequency fs of a pulse wave in relation to the spectrum (FIG. 6) obtained from the processed signal through frequency analysis becomes clearer than the spectrum (FIG. 5) obtained through frequency analysis performed before processing. Hence, a pulse rate can be computed by a pulse rate=fs×60 [beats/min.].

(How to Determine Whether Noise is Mixed into Observation Signal)

An observation signal is separated into signals each associated with one of predetermined frequency ranges which are divided. The division of the observed frequency band may be performed for consecutive frequency ranges or discrete ranges.

In each frequency range, an infrared light component is taken as a horizontal axis (or a vertical axis), and a red light component is taken as the axis orthogonal to the horizontal axis (or the vertical axis).

Figure 7:
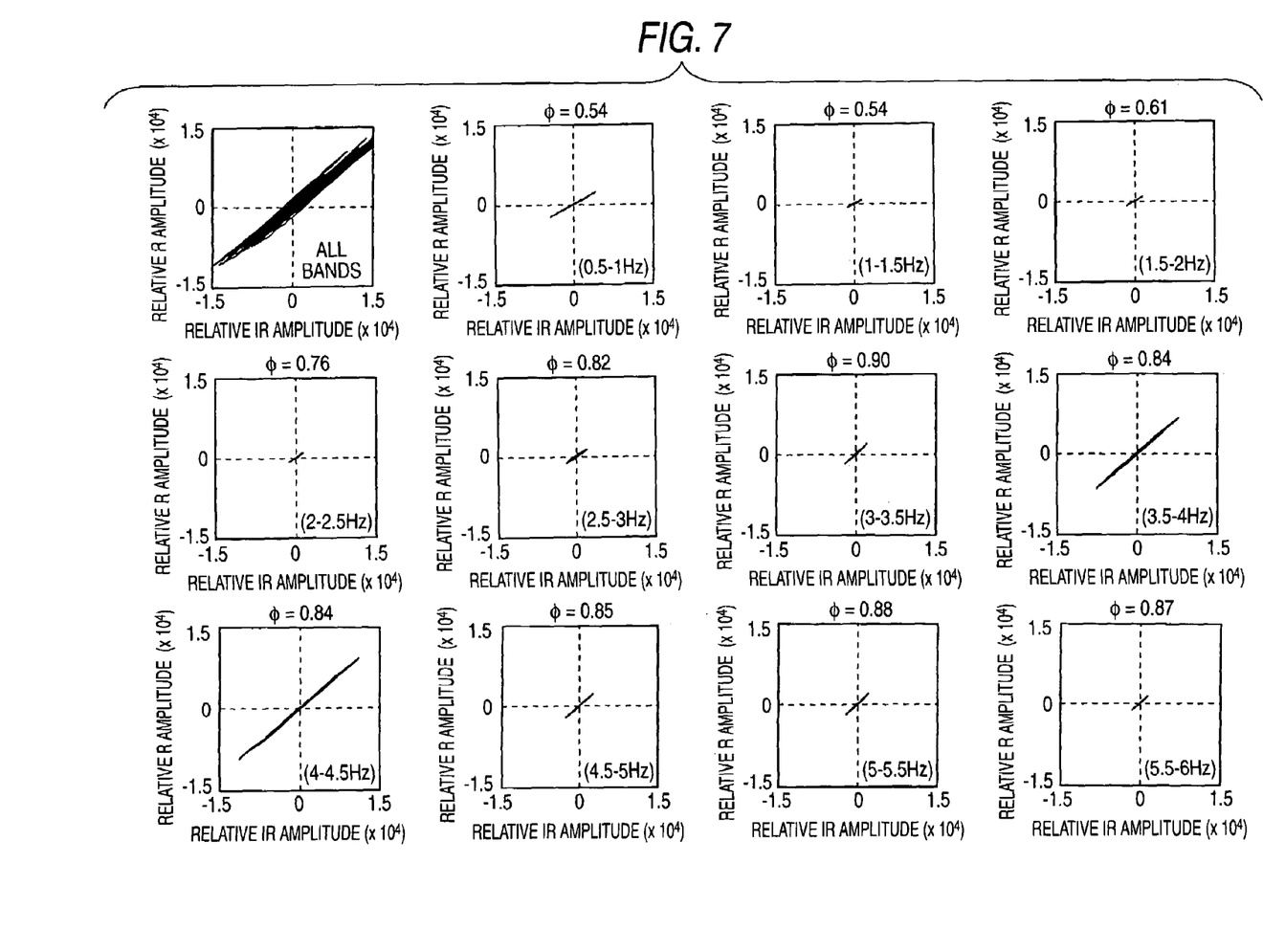
FIG. 7 shows graphs plotted in the same way as that in FIG. 2B for every divided frequency ranges, in a case where noise is superimposed on an observation signal.

FIG. 7 shows graphs plotted with the infrared light component being taken as the horizontal axis and the red light component being taken as the vertical axis.

A gradient corresponding to the principal component of the graph is determined over the entire pulse wave frequency range ("all bands" shown in FIGS. 7 and 8) and for each frequency range obtained after separation. The observation signal is determined to be a single signal or the sum of a plurality of signals, on the basis of whether a match exists between the gradients.

Specifically, a method for determining whether an observation signal is a single signal is to determine whether the gradient of the entire pulse wave frequency band and the gradients of all the separated frequency range fall within a predetermined range, or whether the gradient of a frequency range having a relatively large power and the gradient of the entire pulse wave frequency band fall within the predetermined range.

Figure 8:
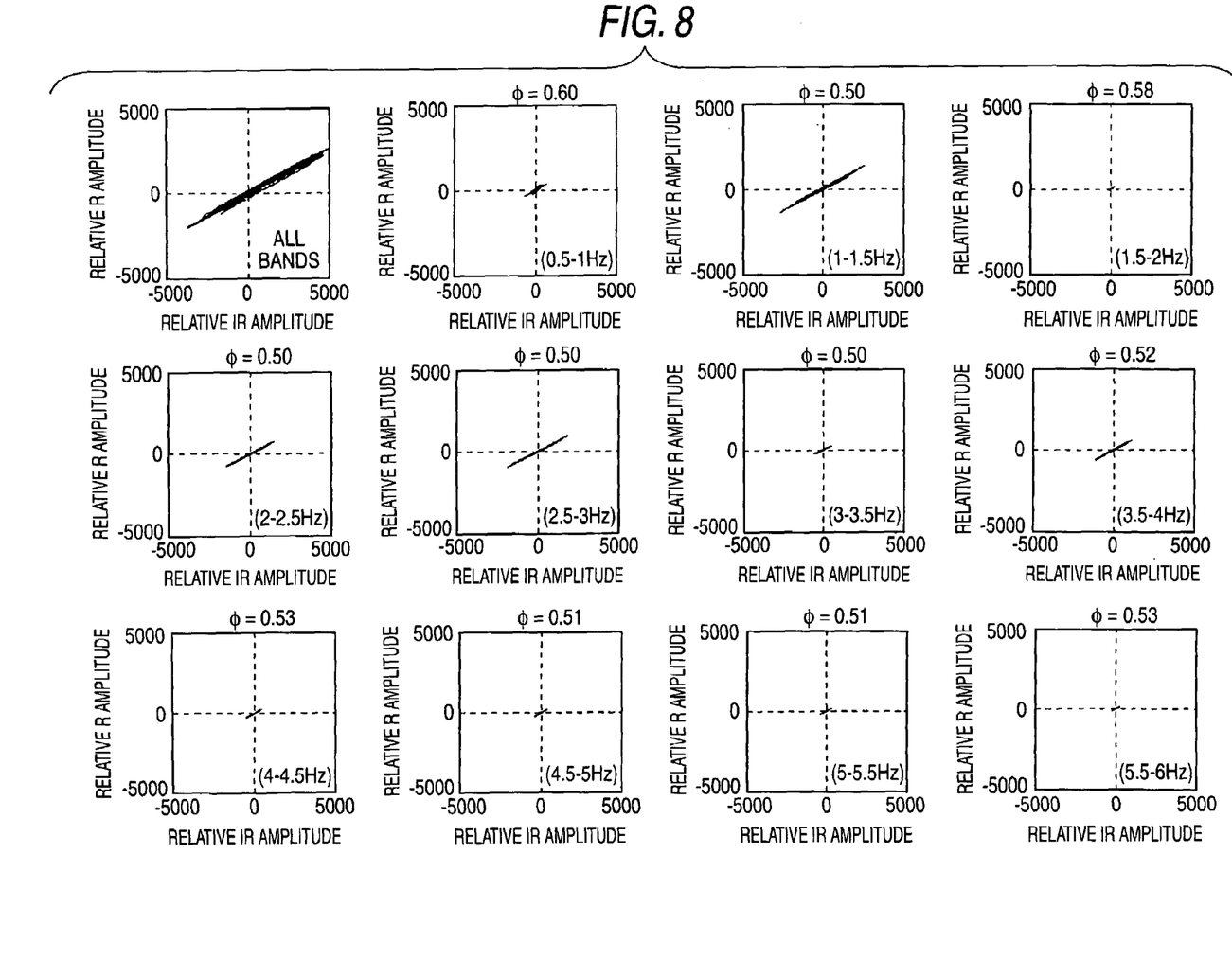
FIG. 8 shows graphs prepared by the principle shown in FIG. 2B for every divided frequency ranges, in a case where noise is not superimposed on an observation signal.

Specifically, FIGS. 7 and 8 show that the entire pulse wave frequency band and the range from 0.5 Hz to 6 Hz are divided in increments of 0.5 Hz. The gradient of the principal component is described at the top of each graph.

FIG. 7 shows different values in ranges having a relatively large power, such as 0.5 to 1 Hz: 0.54, 3.5 to 4.0 Hz: 0.84, and 4.0 to 4.5 Hz: 0.84. Summation of a plurality of signals can be determined to be observed.

FIG. 8 shows a value of 0.50 is exhibited in a range of 1 to 1.5 Hz, a range of 2 to 2.5 Hz, and a range of 2.5 to 3 Hz, each having a relatively large power. Hence, the observation signal is determined to be a single signal.

(Computation of Candidate for Oxygen Saturation)

The pulse wave signal frequency band is divided into a plurality of ranges, as in the case of determination of mixing of noise. Independent component analysis is performed for each of the thus-separated frequency ranges.

Under the assumption that a longitudinal vector of the observation signal is taken as X and a transposed matrix is taken as T, the following equation is derived from Equations 11 and 12.

$$X = (X_0, X_1, X_2, \ldots)^T \quad (21)$$

$$(X_i) = \begin{pmatrix} IR_i \\ R_i \end{pmatrix} (i = 0, 1, 2, \ldots) \quad (22)$$

A variance-covariance matrix H of the longitudinal vector X of the observation signal is expressed as:

$$H = X^T \cdot X \quad (23)$$

A diagonal matrix having eigenvalues as diagonal elements is taken as $\Lambda$, and a matrix formed from eigenvectors is taken as $\Gamma$. Provided that the transformation matrix is taken as U, the independent component Y is obtained as:

$$Y = U \cdot X = \Gamma \cdot \Lambda^{-\frac{1}{2}} \cdot \Gamma^T \cdot X \quad (24)$$

The independent component Y is dissolved into independent components.

If signal components are present in the thus-separated frequency ranges, the signal components can be converted into a signal component-noise component plane such as that shown in FIG. 3C.

If the matrix formed from eigenvectors is converted through use of an inverse matrix $U^{-1}$ of the transformation matrix U, a vector is projected onto the IR-R plane. The gradient of the vector expressing the signal component is obtained as $\Phi s$, and the gradient of the vector representing the noise component is obtained as $\Phi n$.

Figure 9:
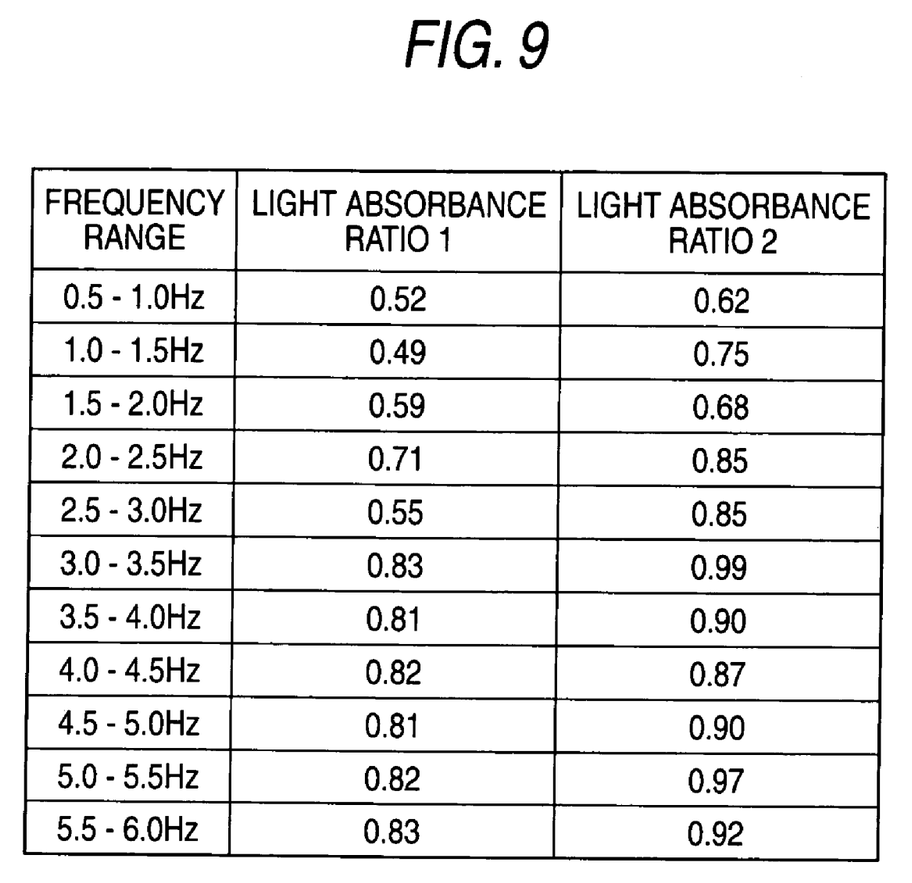
FIG. 9 shows a result obtained by determining a gradient for each of the frequency ranges shown in FIG. 7, through independent component analysis.
Figure 10:
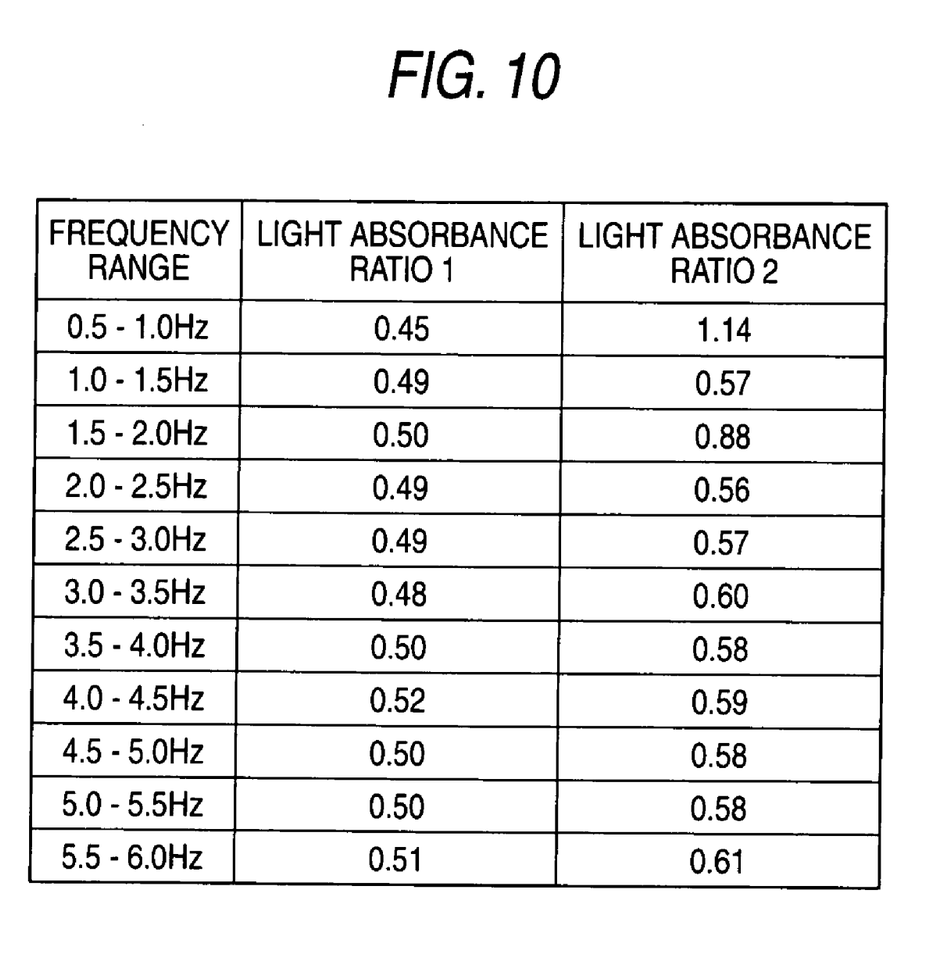
FIG. 10 shows a result obtained by determining a gradient for each of the frequency ranges shown in FIG. 8, through the independent component analysis.

FIG. 10 shows results of determination of the gradient of the observation signal shown in FIG. 2 on each of the frequency ranges shown in FIG. 8. The light absorbance ratios 1 are understood to be close to each other over the respective frequencies (i.e., 0.5±0.02). FIG. 9 shows results obtained by processing the graphs shown in FIG. 7, and a result showing $\Phi s$ is obtained within a range including fs shown in FIG. 6. The oxygen saturation $SpO_2$ is obtained as a function of $\Phi s$; that is, $SpO_2 = f(\Phi s)$.

Figure 11:
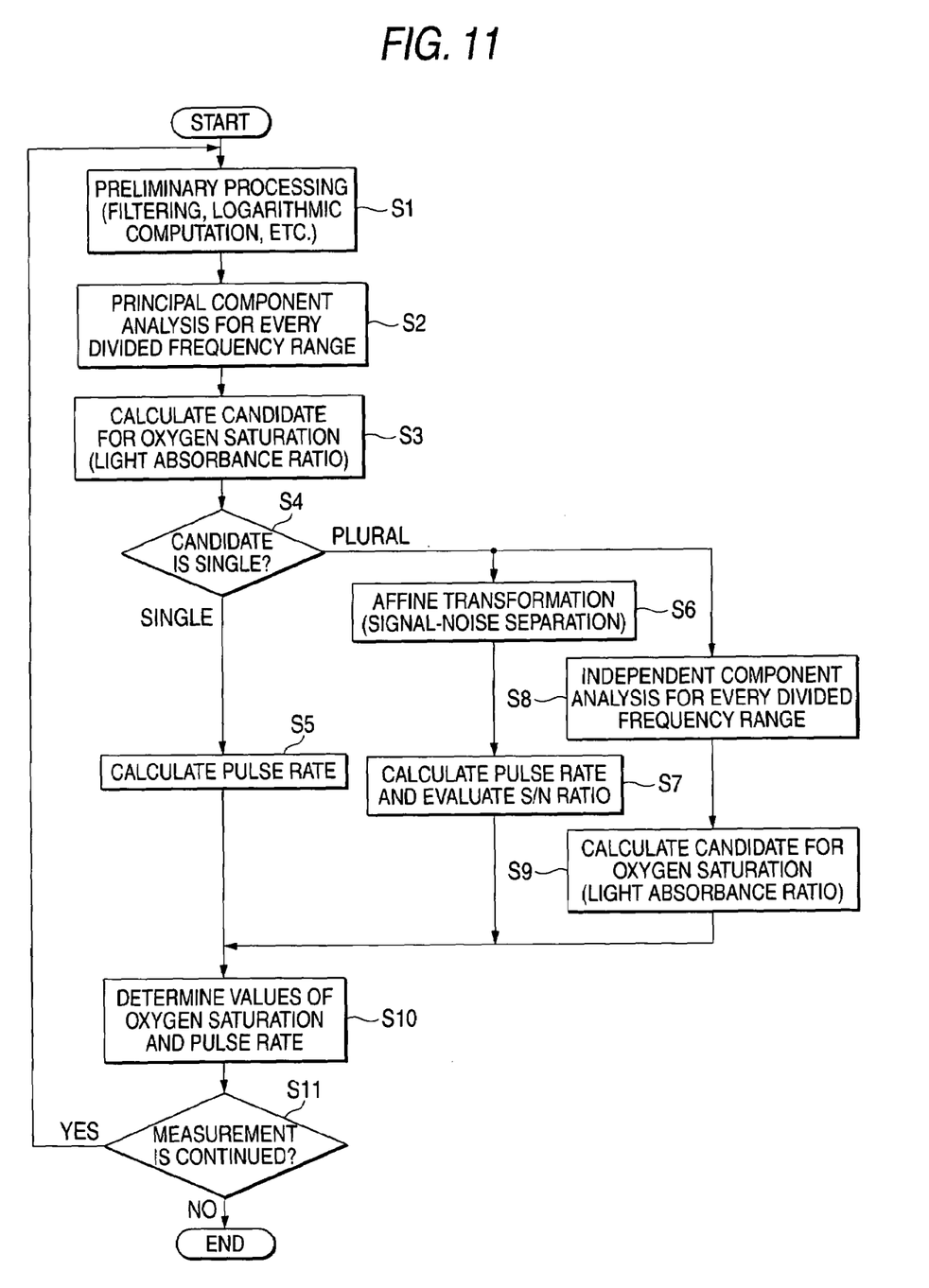
FIG. 11 is a flowchart showing a processing flow performed in the pulse oximeter shown in FIG. 1.

Operation of the processor of the device block shown in FIG. 1 will now be described in detail with reference to FIG. 11.

When measurement is commenced, digital signals obtained as a result of observation of infrared light and red light are subjected to preliminary processing (step S1). Here, the preliminary processing refers to logarithmic computation or pulse wave band filtering on the basis of the Lambert-Beer law.

The signals are divided into predetermined frequency ranges (e.g., in increments of 0.5 Hz) through use of band-pass filters, thereby determining a principal component of light absorbance ratio (i.e., the gradient of the principal component on an IR-R plane) for each frequency range (step S2).

Whether a match exists between the gradients determined for the respective frequency ranges is determined, thereby determining a candidate for a light absorbance ratio of a pulse wave (step S3). A plurality of candidates may be acceptable.

A determination is made as to whether the candidate (signal source) is single or plural (step S4), on the basis of the results obtained in the step S2.

In a case where the determination is single, oxygen saturation is determined from the principal component light absorbance ratio, and the fundamental cycle is determined from the result obtained in the step S1. Thus, a pulse rate is computed (step S5).

In a case where the determination is plural, at the step S6, affine transformation is performed through use of the candidates for the light absorbance ratio obtained in the step S3 or the result of the light absorbance ratios corresponding to an immediately-preceding $SpO_2$ value (sufficiently shorter than the pulse rate: for example, 10 msec faster), or a light absorbance ratio which has been determined that the noise is not mixed therein. Equation 19 is used for the transformation matrix, and the matrix is rotated with reference to $\phi$ (i.e., a value corresponding to a light absorbance ratio), and $\theta$ is determined as an angle at which a norm value in the direction of the $\phi$ axis becomes minimum.

In order to identify a pulse rate, the fundamental cycle Ts (see FIG. 3D) is determined from a cycle determined along the time axis of the signal obtained in the direction of $\phi$ determined in the step S6, or the frequency analysis is performed to identify the fundamental frequency fs (see FIG. 6). A signal-to-noise (S/N) ratio is determined for each frequency, and the thus-determined ratio is taken as one index for evaluating the reliability of the obtained light absorbance ratio (step S7).

On the other hand, time domain data for the respective frequency ranges, which are divided at the step S2, are used to perform independent component analysis (step S8).

The gradients at the IR-R plane of the eigenvectors obtained in the step S8 are determined, and it is checked whether a match exists between the frequency ranges, to thus determine a candidate for a light absorbance ratio (step S9). A plurality of candidates may be acceptable.

Outputs obtained in the steps S3, S5, S7, and S9 are compared with the light absorbance ratio and bands obtained in the past. Current oxygen saturation is determined from a common item, consistency, and reliability (output from the step S7). The oxygen saturation is averaged, as required, and the thus-averaged oxygen saturation is output (step S10).

When measurement is performed continuously, processing returns to the step S1, and processing is iterated. If measurement is not performed continuously, measurement is terminated.

According to the invention, the pulse wave signal is separated from the noise signal through use of a known light absorbance ratio, thereby acquiring a pulse wave signal whose noise has been reduced.

affine transformation is used for utilization of a known light absorbance ratio, thereby whitening an observation signal. The pulse wave signal is separated from the noise signal. Thus, a pulse wave signal whose noise has been reduced can be acquired.

The pulse wave signal frequency band is divided into a plurality of frequency ranges. The principal component of the light absorbance ratio is determined for each frequency band. By judging whether a match exists between the light absorbance ratios, a determination can be made as to whether noise is mixed into the observation signal.

The affine transformation utilizing a known light absorbance ratio enables determination of a first rotation utilizing a known light absorbance ratio and a coefficient suitable for reducing noise. Thus, a pulse wave signal whose noise has been reduced can be acquired.

A pulse can be detected from the pulse wave signal whose noise has been reduced, or a pulse rate can be determined through frequency analysis of the pulse wave signal.

Dividing the pulse wave signal frequency band into a plurality of frequency ranges enables a reduction in the number of signal sources. Further, performing whitening operation on a per-frequency-range basis enables determination of a light absorbance ratio of the pulse wave signal and a light absorbance ratio of the noise signal Since the pulse wave signal is separated from the noise signal, an S/N ratio is obtained for each divided frequency range, and the thus-obtained S/N ratio can be utilized as an index to be used for evaluating a signal.

What is claimed is:

1. A method of processing an observed pulse wave data, comprising steps of:
   irradiating a living body with a first light beam having a first wavelength and a second light beam having a second wavelength which is different from the first wavelength;
   converting the first light beam and the second light beam, which have been reflected or transmitted from the living body, into a first electric signal corresponding to the first wavelength and a second electric signal corresponding to the second wavelength, as the observed pulse wave data;
   dividing a frequency band of the observed pulse wave data into a plurality of frequency ranges;
   computing a light absorbance ratio obtained from the first electric signal and the second electric signal, for each one of the divided frequency ranges; and
   determining that noise is not mixed into the observed pulse wave data in a case where a substantial match exists among light absorbance ratios computed for the respective frequency ranges.

2. The signal processing method as set forth in claim 1, wherein the existence of the substantial match of the light absorbance ratios is determined with regard to frequency ranges in which at least one of the first electric signal and the second electric signal has relatively large powers.

3. A method of processing an observed pulse wave data, comprising steps of:
   irradiating a living body with a first light beam having a first wavelength and a second light beam having a second wavelength which is different from the first wavelength;
   converting the first light beam and the second light beam, which have been reflected or transmitted from the living body, into a first electric signal corresponding to the first wavelength and a second electric signal corresponding to the second wavelength, as the observed pulse wave data; and
   whitening the first electric signal and the second electric signal by an affine transformation using a known light absorbance ratio, in order to separate a pulse signal component and a noise component which are contained in the observed pulse wave data.

4. The signal processing method as set forth in claim 3, wherein the affine transformation is performed with the following equation:

$$\begin{pmatrix} S \\ N \end{pmatrix} = \begin{pmatrix} 1 & -\frac{1}{\tan\theta} \\ 0 & \frac{1}{\sin\theta} \end{pmatrix} \begin{pmatrix} \cos\phi & \sin\phi \\ -\sin\phi & \cos\phi \end{pmatrix} \begin{pmatrix} s1 \\ s2 \end{pmatrix}$$

where, S is the pulse signal component, N is the noise component, s1 is the first electric signal, s2 is the second electric signal, $\phi = \tan^{-1} \Phi$, $\Phi$ is the known light absorbance ratio, and $\theta$ is a value selected from a range of $-\phi$ to $(\pi/2-\phi)$, and
   wherein $\theta$ is so selected as to make a norm of the pulse signal component minimum.

5. The signal processing method as set forth in claim 3, further comprising steps of:
   dividing a frequency band of the observed pulse wave data into a plurality of frequency ranges;
   computing a light absorbance ratio obtained from the first electric signal and the second electric signal, for each one of the divided frequency ranges; and
   determining that noise is not mixed into the observed pulse wave data in a case where a substantial match exists among light absorbance ratios computed for the respective frequency ranges,
   wherein one of the light absorbance ratios, which are determined that the noise is not mixed therein, is used as the known light absorbance ratio.

6. The signal processing method as set forth in claim 3, further comprising a step of obtaining a signal-to-noise ratio of the observed pulse wave data by performing a frequency analysis with respect to the pulse signal component and the noise component at each of predetermined frequencies.

7. The signal processing method as set forth in claim 3, further comprising a step of displaying a pulse wave of the living body, based on the pulse signal component.

8. The signal processing method as set forth in claim 3, further comprising a step of calculating a pulse rate of the living body based on the pulse signal component.

9. A method of processing an observed pulse wave data, comprising steps of:
   irradiating a living body with a first light beam having a first wavelength and a second light beam having a second wavelength which is different from the first wavelength;
   converting the first light beam and the second light beam, which have been reflected or transmitted from the living body, into a first electric signal corresponding to the first wavelength and a second electric signal corresponding to the second wavelength, as the observed pulse wave data;

dividing a frequency band of the observed pulse wave data into a plurality of frequency ranges; and whitening the first electric signal and the second electric signal to separate a pulse signal component and a noise component which are contained in the observed pulse wave data, for each one of the divided frequency ranges.

10. The signal processing method as set forth in claim 9, wherein the step of whitening the first electric signal and the second electric signal is performed with independent component analysis.

11. The signal processing method as set forth in claim 9, further comprising a step of obtaining a signal-to-noise ratio of the observed pulse wave data by performing a frequency analysis with respect to the signal component and the noise component at each one of the frequency ranges.

12. A pulse photometer comprising:
a first light source adapted to irradiate a living body with a first light beam having a first wavelength;
a second light source adapted to irradiate the living body with a second light beam having a second waveform which is different from the first wavelength;
a converter operable to convert the first light beam and the second light beam subsequent to irradiating the living body to a first and second electrical signals, respectively, as observed data;
a processor operable to divide a frequency band of the observed data into a plurality of frequency ranges, compute a light absorption ratio based on the first and second electrical signals for each one of the divided frequency ranges, and determine that noise is not mixed in the observed data in case where a substantial match exists among light absorbance ratios computed for the respective range of frequencies.

13. A pulse photometer comprising:
a first light source adapted to irradiate a living body with a first light beam having a first wavelength;
a second light source adapted to irradiate the living body with a second light beam having a second waveform which is different from the first wavelength;
a converter operable to convert the first light beam and the second light beam subsequent to irradiating the living body to a first and second electrical signals, respectively, as observed pulse wave data;
a processor operable to whiten the first and the second electrical signals by affine transformation using a known light absorbance ratio to separate a pulse signal component and a noise component contained in the observed pulse wave data.

14. A pulse photometer, comprising:
a first light source adapted to irradiate a living body with a first light beam having a first wavelength;
a second light source adapted to irradiate the living body with a second light beam having a second waveform which is different from the first wavelength;
a converter operable to convert the first light beam and the second light beam subsequent to irradiating the living body to a first and second electrical signals, respectively, as observed data;
a processor operable to divide a frequency band of the observed data into a plurality of frequency ranges, and whiten the first and the second electrical signals to separate a pulse signal component and a noise component contained in the observed data for each one of the divided frequency ranges.

* * * * *